(12) United States Patent
Sowards et al.

(10) Patent No.: US 12,287,520 B2
(45) Date of Patent: Apr. 29, 2025

(54) OPTICAL CONNECTION SYSTEMS AND METHODS THEREOF

(71) Applicant: Bard Access Systems, Inc., Salt Lake City, UT (US)

(72) Inventors: Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 14 days.

(21) Appl. No.: 18/141,289

(22) Filed: Apr. 28, 2023

(65) Prior Publication Data

US 2023/0266543 A1    Aug. 24, 2023

Related U.S. Application Data

(63) Continuation of application No. 17/967,794, filed on Oct. 17, 2022, now Pat. No. 11,638,536, which is a
(Continued)

(51) Int. Cl.
*H04B 10/00* (2013.01)
*A61B 5/06* (2006.01)
(Continued)

(52) U.S. Cl.
CPC ............ *G02B 6/4202* (2013.01); *A61B 5/065* (2013.01); *A61M 25/0111* (2013.01);
(Continued)

(58) Field of Classification Search
CPC .. G02B 6/4202; G02B 6/4274; G02B 6/4292; G02B 6/4201; A61B 5/7465;
(Continued)

(56) References Cited

U.S. PATENT DOCUMENTS 3,493,288 A    2/1970  Oltman et al.
4,768,855 A    9/1988  Nishi et al.
(Continued)

FOREIGN PATENT DOCUMENTS

CA        3025240 A1      11/2017
DE   102016109601 A1      11/2017
(Continued)

OTHER PUBLICATIONS

Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide- coated multicore optical fiber," Opt. Express 27, 38421-38434 (2019). (Year: 2019).
(Continued)

*Primary Examiner* — Agustin Bello
(74) *Attorney, Agent, or Firm* — Rutan & Tucker LLP

(57) ABSTRACT

Optical connection systems including electrical-and-optical connection systems and methods thereof are disclosed. An electrical-and-optical connection system can include an extension tube having a plug and a relay module having a receptacle. The plug can be formed of a metal piece around electrical wires, which, in turn, are around optical-fiber cores that extend along a length of the extension tube. The plug can be configured to pierce through at least a sterile barrier. The relay module can include electrical wires and optical-fiber cores within a housing of the relay module, as well as a receptacle disposed in the housing. The receptacle can be configured to simultaneously accept insertion of the plug therein and establish both electrical and optical connections between the plug and the receptacle from a sterile field to a non-sterile field set up by the sterile barrier. Shape-sensing systems including the optical connection systems are also disclosed.

11 Claims, 7 Drawing Sheets

Related U.S. Application Data continuation of application No. 17/185,777, filed on Feb. 25, 2021, now Pat. No. 11,474,310.

(60) Provisional application No. 62/983,402, filed on Feb. 28, 2020.

(51) Int. Cl.
*A61M 25/01* (2006.01)
*G02B 6/42* (2006.01)
*A61B 5/00* (2006.01)

(52) U.S. Cl.
CPC .......... *G02B 6/4274* (2013.01); *G02B 6/4292* (2013.01); *A61B 5/7465* (2013.01); *A61M 2205/3592* (2013.01)

(58) Field of Classification Search
CPC ...... A61B 2562/0233; A61B 2562/227; A61B 2562/228; A61B 5/065
See application file for complete search history.

(56) References Cited

U.S. PATENT DOCUMENTS

| | | | |
|---|---|---|---|
| 4,813,429 A * | 3/1989 | Eshel | A61M 25/10 607/102 |
| 5,099,845 A | 3/1992 | Besz et al. | |
| 5,163,935 A * | 11/1992 | Black | A61N 5/0601 606/7 |
| 5,178,153 A | 1/1993 | Einzig | |
| 5,207,672 A * | 5/1993 | Roth | A61B 18/24 606/7 |
| 5,211,165 A | 5/1993 | Dumoulin et al. | |
| 5,220,703 A | 6/1993 | Kanayama et al. | |
| 5,275,151 A * | 1/1994 | Shockey | A61M 25/0136 604/95.04 |
| 5,295,212 A * | 3/1994 | Morton | G02B 6/3886 385/24 |
| 5,423,321 A | 6/1995 | Fontenot | |
| 5,454,807 A * | 10/1995 | Lennox | A61B 18/24 606/17 |
| 5,517,997 A | 5/1996 | Fontenot | |
| 5,599,492 A | 2/1997 | Engelson | |
| 5,622,170 A | 4/1997 | Schulz | |
| 5,633,494 A | 5/1997 | Danisch | |
| 5,693,043 A | 12/1997 | Kittrell et al. | |
| 5,740,808 A * | 4/1998 | Panescu | A61B 5/6853 600/585 |
| 5,827,313 A * | 10/1998 | Ream | A61B 8/4209 606/171 |
| 5,872,879 A * | 2/1999 | Hamm | G02B 6/3604 385/25 |
| 5,873,842 A | 2/1999 | Brennen et al. | |
| 5,879,306 A | 3/1999 | Fontenot et al. | |
| 5,906,579 A | 5/1999 | Vander Salm et al. | |
| 5,957,831 A * | 9/1999 | Adair | A61B 1/00052 600/101 |
| 6,069,698 A * | 5/2000 | Ozawa | G01B 9/02064 356/511 |
| 6,081,741 A | 6/2000 | Hollis | |
| 6,178,346 B1 | 1/2001 | Amundson et al. | |
| 6,208,887 B1 | 3/2001 | Clarke | |
| 6,210,362 B1 | 4/2001 | Ponzi | |
| 6,319,227 B1 * | 11/2001 | Mansouri-Ruiz | A61B 8/4461 604/95.01 |
| 6,343,227 B1 | 1/2002 | Crowley | |
| 6,398,721 B1 | 6/2002 | Nakamura et al. | |
| 6,485,482 B1 * | 11/2002 | Belef | A61B 8/12 604/164.08 |
| 6,564,089 B2 * | 5/2003 | Izatt | G01B 9/02002 600/478 |
| 6,593,884 B1 | 7/2003 | Gilboa et al. | |
| 6,597,941 B2 * | 7/2003 | Fontenot | A61B 1/0655 600/476 |
| 6,619,857 B2 | 9/2003 | Miyake | |
| 6,650,923 B1 | 11/2003 | Lesh et al. | |
| 6,685,666 B1 * | 2/2004 | Fontenot | A61B 5/6848 600/478 |
| 6,687,010 B1 * | 2/2004 | Horii | G01B 9/0205 356/479 |
| 6,690,966 B1 | 2/2004 | Rava et al. | |
| 6,701,181 B2 | 3/2004 | Tang et al. | |
| 6,711,426 B2 | 3/2004 | Benaron et al. | |
| 6,816,743 B2 | 11/2004 | Moreno et al. | |
| 6,892,090 B2 | 5/2005 | Verard et al. | |
| 6,895,267 B2 | 5/2005 | Panescu et al. | |
| 6,975,803 B2 | 12/2005 | Koide et al. | |
| 7,132,645 B2 | 11/2006 | Kom | |
| 7,273,056 B2 | 9/2007 | Wilson et al. | |
| 7,344,533 B2 * | 3/2008 | Pearson | A61B 18/1477 606/41 |
| 7,366,562 B2 | 4/2008 | Dukesherer et al. | |
| 7,366,563 B2 | 4/2008 | Kleen et al. | |
| 7,396,354 B2 | 7/2008 | Rychnovsky et al. | |
| 7,406,346 B2 | 7/2008 | Kleen et al. | |
| 7,515,265 B2 | 4/2009 | Alfano et al. | |
| 7,532,920 B1 | 5/2009 | Ainsworth et al. | |
| 7,587,236 B2 | 9/2009 | Demos et al. | |
| 7,603,166 B2 * | 10/2009 | Casscells, III | A61B 1/046 600/476 |
| 7,699,855 B2 * | 4/2010 | Anderson | A61B 34/30 606/1 |
| 7,729,735 B1 | 6/2010 | Burchman | |
| 7,757,695 B2 | 7/2010 | Wilson et al. | |
| 7,758,499 B2 | 7/2010 | Adler | |
| 7,840,253 B2 | 11/2010 | Tremblay et al. | |
| 7,992,573 B2 * | 8/2011 | Wilson | A61B 5/06 600/407 |
| 8,032,200 B2 | 10/2011 | Tearney et al. | |
| 8,054,469 B2 * | 11/2011 | Nakabayashi | G01N 21/4795 356/479 |
| 8,060,187 B2 * | 11/2011 | Marshik-Geurts | A61B 5/0086 600/478 |
| 8,073,517 B1 * | 12/2011 | Burchman | A61B 5/14542 600/341 |
| 8,078,261 B2 | 12/2011 | Imam | |
| 8,187,189 B2 | 5/2012 | Jung et al. | |
| 8,197,494 B2 * | 6/2012 | Jaggi | A61B 5/06 606/130 |
| 8,267,932 B2 | 9/2012 | Baxter et al. | |
| 8,369,932 B2 | 2/2013 | Cinbis et al. | |
| 8,388,541 B2 | 3/2013 | Messerly et al. | |
| 8,571,640 B2 | 10/2013 | Holman | |
| 8,597,315 B2 * | 12/2013 | Snow | A61B 17/320783 606/159 |
| 8,700,358 B1 | 4/2014 | Parker, Jr. | |
| 8,781,555 B2 * | 7/2014 | Burnside | A61B 46/00 600/585 |
| 8,798,721 B2 | 8/2014 | Dib | |
| 8,968,331 B1 | 3/2015 | Sochor | |
| 8,979,871 B2 * | 3/2015 | Tyc | G01R 33/285 606/130 |
| 9,119,551 B2 * | 9/2015 | Qi | A61B 8/0841 |
| 9,186,046 B2 | 11/2015 | Ramamurthy et al. | |
| 9,339,206 B2 * | 5/2016 | Grunwald | A61B 5/283 |
| 9,345,510 B2 | 5/2016 | Patel et al. | |
| 9,360,630 B2 * | 6/2016 | Jenner | G02B 6/3604 |
| 9,549,685 B2 * | 1/2017 | Cox | A61B 5/061 |
| 9,560,954 B2 * | 2/2017 | Jacobs | A61B 1/00128 |
| 9,572,492 B2 | 2/2017 | Simpson et al. | |
| 9,622,706 B2 * | 4/2017 | Dick | A61B 5/0062 |
| 9,645,326 B1 | 5/2017 | Sausse et al. | |
| 9,649,048 B2 * | 5/2017 | Cox | A61B 8/0841 |
| 9,678,275 B1 * | 6/2017 | Griffin | G02B 6/262 |
| 9,678,284 B2 | 6/2017 | Coggi et al. | |
| 9,872,978 B1 | 1/2018 | Zaborsky et al. | |
| 10,231,643 B2 * | 3/2019 | Grunwald | A61B 5/347 |
| 10,231,753 B2 | 3/2019 | Burnside et al. | |
| 10,258,240 B1 | 4/2019 | Eberle et al. | |
| 10,265,133 B1 * | 4/2019 | McClellan | A61B 46/23 |
| 10,327,830 B2 * | 6/2019 | Grant | A61B 18/02 |
| 10,349,890 B2 * | 7/2019 | Misener | A61B 5/6852 |

(56) References Cited

U.S. PATENT DOCUMENTS

| | | | |
|---|---|---|---|
| 10,448,837 B2* | 10/2019 | Manzke | A61B 1/00045 |
| 10,492,876 B2* | 12/2019 | Anastassiou | A61B 18/201 |
| 10,568,586 B2* | 2/2020 | Begin | A61B 8/465 |
| 10,603,126 B2* | 3/2020 | Karguth | A61B 46/10 |
| 10,620,386 B2 | 4/2020 | Van Der Mark et al. | |
| 10,631,718 B2* | 4/2020 | Petroff | A61B 17/00234 |
| 10,932,670 B2 | 3/2021 | Smith et al. | |
| 10,939,889 B2* | 3/2021 | Flexman | A61B 6/4441 |
| 10,992,078 B2 | 4/2021 | Thompson et al. | |
| 10,992,079 B2* | 4/2021 | Stats | A61B 5/283 |
| 11,000,207 B2* | 5/2021 | Burnside | A61B 5/066 |
| 11,000,265 B1 | 5/2021 | Ryu et al. | |
| 11,103,321 B2* | 8/2021 | Braun | A61B 34/37 |
| 11,123,047 B2* | 9/2021 | Jaffer | A61B 8/5261 |
| 11,259,892 B2* | 3/2022 | Hufford | A61B 46/10 |
| 11,284,916 B2 | 3/2022 | Patel et al. | |
| 11,382,653 B2 | 7/2022 | Patel et al. | |
| 11,474,310 B2* | 10/2022 | Sowards | A61B 5/065 |
| 11,525,670 B2* | 12/2022 | Messerly | G01B 11/165 |
| 11,547,282 B2* | 1/2023 | Weise | A61B 1/00114 |
| 11,607,150 B2* | 3/2023 | Schweikert | A61B 5/282 |
| 11,621,518 B2* | 4/2023 | Stats | H01R 13/6683 |
| | | | 439/131 |
| 11,707,205 B2* | 7/2023 | Messerly | A61B 5/06 |
| | | | 600/374 |
| 11,806,096 B2* | 11/2023 | Flatt | A61B 46/10 |
| 11,850,073 B2 | 12/2023 | Wright et al. | |
| 11,931,112 B2 | 3/2024 | Thompson et al. | |
| 2002/0019627 A1 | 2/2002 | Maguire et al. | |
| 2002/0087206 A1 | 7/2002 | Hirschberg et al. | |
| 2002/0166190 A1 | 11/2002 | Miyake et al. | |
| 2002/0188285 A1 | 12/2002 | Brown | |
| 2002/0198457 A1 | 12/2002 | Tearney et al. | |
| 2003/0045798 A1 | 3/2003 | Hular et al. | |
| 2003/0092995 A1 | 5/2003 | Thompson | |
| 2004/0111020 A1 | 6/2004 | Long | |
| 2004/0111147 A1 | 6/2004 | Rabkin et al. | |
| 2004/0242995 A1 | 12/2004 | Maschke | |
| 2004/0260182 A1 | 12/2004 | Zuluaga et al. | |
| 2005/0033264 A1 | 2/2005 | Redinger | |
| 2006/0013523 A1 | 1/2006 | Childlers et al. | |
| 2006/0036164 A1 | 2/2006 | Wilson et al. | |
| 2006/0100610 A1 | 5/2006 | Wallace et al. | |
| 2006/0189959 A1 | 8/2006 | Schneiter | |
| 2006/0200049 A1 | 9/2006 | Leo et al. | |
| 2006/0241395 A1 | 10/2006 | Kruger et al. | |
| 2006/0241492 A1 | 10/2006 | Boese et al. | |
| 2007/0060847 A1 | 3/2007 | Leo et al. | |
| 2007/0156019 A1 | 7/2007 | Larkin et al. | |
| 2007/0179485 A1 | 8/2007 | Yeik et al. | |
| 2007/0201793 A1 | 8/2007 | Askins et al. | |
| 2007/0253673 A1 | 11/2007 | Nielsen et al. | |
| 2007/0287886 A1 | 12/2007 | Saadat | |
| 2007/0299425 A1 | 12/2007 | Waner et al. | |
| 2008/0034519 A1 | 2/2008 | Fujiwara | |
| 2008/0172119 A1 | 7/2008 | Yamasaki et al. | |
| 2008/0183128 A1 | 7/2008 | Morriss et al. | |
| 2008/0281293 A1 | 11/2008 | Peh et al. | |
| 2008/0285909 A1 | 11/2008 | Younge et al. | |
| 2009/0005675 A1* | 1/2009 | Grunwald | A61B 5/349 |
| | | | 600/467 |
| 2009/0018393 A1 | 1/2009 | Dick et al. | |
| 2009/0046980 A1 | 2/2009 | Rohlen | |
| 2009/0062634 A1 | 3/2009 | Say et al. | |
| 2009/0137952 A1 | 5/2009 | Ramamurthy et al. | |
| 2009/0208143 A1 | 8/2009 | Yoon et al. | |
| 2009/0227992 A1 | 9/2009 | Nir et al. | |
| 2009/0234328 A1* | 9/2009 | Cox | A61B 8/0841 |
| | | | 600/509 |
| 2009/0253967 A1 | 10/2009 | Gill et al. | |
| 2009/0304582 A1 | 12/2009 | Rousso et al. | |
| 2009/0318757 A1 | 12/2009 | Singh | |
| 2009/0324161 A1 | 12/2009 | Prisco | |
| 2010/0016729 A1 | 1/2010 | Futrell | |
| 2010/0030063 A1* | 2/2010 | Lee | A61B 5/06 |
| | | | 600/424 |
| 2010/0063534 A1 | 3/2010 | Kugler et al. | |
| 2010/0114115 A1 | 5/2010 | Schlesinger et al. | |
| 2010/0114190 A1 | 5/2010 | Bendett et al. | |
| 2010/0139669 A1* | 6/2010 | Piferi | A61B 46/23 |
| | | | 128/852 |
| 2010/0204569 A1* | 8/2010 | Burnside | A61B 5/0833 |
| | | | 604/272 |
| 2010/0286531 A1 | 11/2010 | Ryan et al. | |
| 2010/0292758 A1 | 11/2010 | Lee et al. | |
| 2011/0087112 A1 | 4/2011 | Leo et al. | |
| 2011/0098533 A1 | 4/2011 | Onoda et al. | |
| 2011/0144481 A1 | 6/2011 | Feer et al. | |
| 2011/0144630 A1 | 6/2011 | Loeb | |
| 2011/0166442 A1 | 7/2011 | Sarvazyan | |
| 2011/0172680 A1 | 7/2011 | Younge et al. | |
| 2011/0178509 A1 | 7/2011 | Zerfas et al. | |
| 2011/0196248 A1* | 8/2011 | Grunwald | A61B 5/339 |
| | | | 600/509 |
| 2011/0245662 A1 | 10/2011 | Eggers et al. | |
| 2011/0295108 A1* | 12/2011 | Cox | A61B 5/06 |
| | | | 600/424 |
| 2012/0046562 A1 | 2/2012 | Powers et al. | |
| 2012/0143029 A1* | 6/2012 | Silverstein | A61B 8/0891 |
| | | | 600/374 |
| 2012/0184827 A1 | 7/2012 | Shwartz et al. | |
| 2012/0184955 A1 | 7/2012 | Pivotto et al. | |
| 2012/0321243 A1 | 12/2012 | Younge et al. | |
| 2013/0096482 A1 | 4/2013 | Bertrand et al. | |
| 2013/0104884 A1* | 5/2013 | Vazales | A61M 16/0463 |
| | | | 128/202.16 |
| 2013/0150732 A1* | 6/2013 | Manzke | A61B 1/00045 |
| | | | 600/478 |
| 2013/0188855 A1 | 7/2013 | Desjardins et al. | |
| 2013/0190741 A1 | 7/2013 | Moll et al. | |
| 2013/0204124 A1 | 8/2013 | Duindam et al. | |
| 2013/0211246 A1 | 8/2013 | Parasher | |
| 2013/0296652 A1 | 11/2013 | Farr | |
| 2013/0296693 A1 | 11/2013 | Wenzel et al. | |
| 2013/0310668 A1 | 11/2013 | Young | |
| 2013/0324840 A1 | 12/2013 | Zhongping et al. | |
| 2014/0031674 A1* | 1/2014 | Newman | A61B 5/283 |
| | | | 600/424 |
| 2014/0046261 A1* | 2/2014 | Newman | A61B 5/062 |
| | | | 604/158 |
| 2014/0058368 A1 | 2/2014 | Hogue | |
| 2014/0088413 A1* | 3/2014 | Von Bucsh | A61B 5/0084 |
| | | | 600/424 |
| 2014/0121468 A1 | 5/2014 | Eichenholz | |
| 2014/0155948 A1 | 6/2014 | Walsh et al. | |
| 2014/0188133 A1* | 7/2014 | Misener | A61B 8/0841 |
| | | | 606/130 |
| 2014/0221829 A1 | 8/2014 | Maitland et al. | |
| 2014/0259477 A1 | 9/2014 | Huang | |
| 2014/0275997 A1 | 9/2014 | Chopra et al. | |
| 2014/0318825 A1 | 10/2014 | Erb et al. | |
| 2014/0378945 A1 | 12/2014 | Beri | |
| 2015/0029511 A1 | 1/2015 | 'T Hooft et al. | |
| 2015/0031987 A1 | 1/2015 | Pameijer et al. | |
| 2015/0045649 A1 | 2/2015 | O'Dea et al. | |
| 2015/0080688 A1 | 3/2015 | Cinbis et al. | |
| 2015/0099979 A1* | 4/2015 | Caves | A61B 5/0071 |
| | | | 600/407 |
| 2015/0105654 A1* | 4/2015 | Meyer | A61B 1/3137 |
| | | | 600/300 |
| 2015/0119700 A1 | 4/2015 | Liang et al. | |
| 2015/0119724 A1 | 4/2015 | Weber et al. | |
| 2015/0209113 A1 | 7/2015 | Burkholz et al. | |
| 2015/0209117 A1* | 7/2015 | Flexman | A61B 34/20 |
| | | | 600/424 |
| 2015/0244465 A1* | 8/2015 | Chou | H05K 3/301 |
| | | | 398/201 |
| 2015/0270900 A1* | 9/2015 | Hilario | H04B 10/40 |
| | | | 398/140 |
| 2015/0301288 A1 | 10/2015 | Thornton, Jr. | |
| 2015/0305816 A1* | 10/2015 | Hadzic | A61B 46/23 |
| | | | 128/852 |

(56) References Cited

U.S. PATENT DOCUMENTS

| | | |
|---|---|---|
| 2015/0320977 A1 | 11/2015 | Vitullo et al. |
| 2016/0018602 A1* | 1/2016 | Govari ............... G02B 6/3826 385/71 |
| 2016/0151115 A1* | 6/2016 | Karguth ............ A61B 1/00149 606/41 |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1* | 12/2016 | Misener ............... A61M 25/01 600/373 |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1* | 3/2017 | Silverstein ........... A61B 8/0841 |
| 2017/0082806 A1* | 3/2017 | Van Der Mark ....... G02B 6/387 |
| 2017/0196479 A1 | 7/2017 | Liu et al. |
| 2017/0201036 A1* | 7/2017 | Cohen ..................... A61B 5/00 |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0303824 A1 | 10/2017 | Schlesinger et al. |
| 2017/0333136 A1* | 11/2017 | Hladio ................ A61B 5/6847 |
| 2017/0348063 A1* | 12/2017 | Braun ..................... A61B 34/30 |
| 2018/0067268 A1 | 3/2018 | Murakami et al. |
| 2018/0095231 A1 | 4/2018 | Lowell et al. |
| 2018/0113038 A1 | 4/2018 | Janabi-Sharifi et al. |
| 2018/0116551 A1* | 5/2018 | Newman ............... A61B 8/0841 |
| 2018/0140170 A1* | 5/2018 | Van Putten ............... G02B 6/32 |
| 2018/0175547 A1* | 6/2018 | Hsu ..................... H04B 10/803 |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2018/0369432 A1 | 12/2018 | Zaborsky |
| 2019/0008376 A1 | 1/2019 | Wortelboer et al. |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1* | 9/2019 | Van Der Mark ..... G02B 6/3866 |
| 2019/0321110 A1 | 10/2019 | Grunwald et al. |
| 2019/0343424 A1* | 11/2019 | Blumenkranz ....... A61B 1/0051 |
| 2019/0357875 A1* | 11/2019 | Qi ........................... A61B 8/06 |
| 2019/0374196 A1 | 12/2019 | Courtney et al. |
| 2020/0046434 A1 | 2/2020 | Graetzel et al. |
| 2020/0155073 A1 | 5/2020 | Hwang et al. |
| 2020/0170724 A1* | 6/2020 | Flatt ...................... A61B 46/10 |
| 2020/0188036 A1 | 6/2020 | Ding et al. |
| 2020/0275827 A1* | 9/2020 | Weise ................ A61B 1/00114 |
| 2020/0305983 A1 | 10/2020 | Yampolsky et al. |
| 2021/0007796 A1 | 1/2021 | Panescu et al. |
| 2021/0030504 A1* | 2/2021 | Thompson ............ A61B 46/23 |
| 2021/0045814 A1 | 2/2021 | Thompson et al. |
| 2021/0154440 A1* | 5/2021 | Misener ................ A61B 34/20 |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1* | 9/2021 | Sowards ............. G02B 6/4274 |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0290315 A1 | 9/2021 | Lampert et al. |
| 2021/0298680 A1* | 9/2021 | Sowards ............... A61B 5/065 |
| 2021/0299879 A1 | 9/2021 | Pinter et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1* | 12/2021 | Cox ..................... A61B 5/063 |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0039632 A1 | 2/2022 | Polejaev et al. |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1* | 8/2022 | Croll ....................... A61N 5/067 |
| 2022/0330891 A1* | 10/2022 | Sowards ............... A61B 34/20 |
| 2023/0082991 A1 | 3/2023 | Sowards et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1* | 11/2023 | Moore ............... H04B 10/1143 |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |
| 2024/0423456 A1 | 12/2024 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 3545849 A1 | 10/2019 |
| EP | 3725252 A1 | 10/2020 |
| WO | 9964099 A1 | 12/1999 |
| WO | 2006080076 A1 | 8/2006 |
| WO | 2006122001 A2 | 11/2006 |
| WO | 2009155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016061431 A1 | 4/2016 |
| WO | 2016193051 A1 | 12/2016 |
| WO | 2018071490 A1 | 4/2018 |
| WO | 2018096491 A1 | 5/2018 |
| WO | 2019037071 A1 | 2/2019 |
| WO | 2019046769 A1 | 3/2019 |
| WO | 2019230713 A1 | 12/2019 |
| WO | 2020142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022031613 A1 | 2/2022 |
| WO | 2022081586 A1 | 4/2022 |
| WO | 2022081723 A1 | 4/2022 |
| WO | 2022109045 A1 | 5/2022 |
| WO | 2022115624 A1 | 6/2022 |

(56) References Cited

FOREIGN PATENT DOCUMENTS

| | | |
|---|---|---|
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/689,773, filed Mar. 8, 2022 Non-Final Office Action dated Mar. 19, 2024.
U.S. Appl. No. 17/697,895, filed Mar. 17, 2022 Notice of Allowance dated May 8, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
U.S. Appl. No. 17/187,536, filed Feb. 26, 2021 Non-Final Office Action dated Dec. 15, 2023.
U.S. Appl. No. 17/535,406, filed Nov. 24, 2021 Non-Final Office Action dated Feb. 15, 2024.
U.S. Appl. No. 17/697,895, filed Mar. 17, 2022 Non-Final Office Action dated Jan. 11, 2024.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
U.S. Appl. No. 17/217,852, filed Mar. 30, 2021 Non Final Office Action dated Jun. 7, 2023.
U.S. Appl. No. 17/499,644, filed Oct. 12, 2021 Restriction Requirement dated Jul. 11, 2023.
U.S. Appl. No. 17/697,895, filed Mar. 17, 2022 Final Office Action dated Aug. 16, 2023.
U.S. Appl. No. 17/697,895, filed Mar. 17, 2022 Non Final Office Action dated Jun. 14, 2023.
PCT/US2022/024934 filed Apr. 14, 2022 International Search Report and Written Opinion dated Jul. 18. 2022.
PCT/US2023/020042 filed Apr. 26, 2023 International Search Report and Written Opinion dated Sep. 26, 2023.
PCT/US2023/025757 filed Jun. 20, 2023 International Search Report and Written Opinion dated Sep. 11, 2023.
PCT/US2023/027527 filed Jul. 12, 2023 International Search Report and Written Opinion dated Oct. 16, 2023.
U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/217,852, filed Mar. 30, 2021 Ex Parte Quayle Action dated Sep. 8, 2023.
U.S. Appl. No. 17/217,852, filed Mar. 30, 2021 Notice of Allowance dated Nov. 7, 2023.
U.S. Appl. No. 17/499,644, filed Oct. 12, 2021 Notice of Allowance dated Sep. 18, 2023.
U.S. Appl. No. 17/535,406, filed Nov. 24, 2021 Restriction Requirement dated Nov. 24, 2023.
U.S. Appl. No. 17/697,895, filed Mar. 17, 2022 Advisory Action dated Sep. 8, 2023.
U.S. Appl. No. 17/217,852, filed Mar. 30, 2021 Restriction Requirement dated Mar. 21, 2023.
PCT/US2021/059755 filed Nov. 17, 2021 International Search Report and Written Opinion dated Apr. 29, 2022.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
PCT/US2021/060849 filed Nov. 24, 2021 International Search Report and Written Opinion dated Mar. 9, 2022.
PCT/US2022/043698 filed Sep. 15, 2022 International Search Report and Written Opinion dated Dec. 19. 2022.
U.S. Appl. No. 17/187,536, filed Feb. 26, 2021 Non-Final Office Action dated May 17, 2023.
U.S. Appl. No. 17/967,794, filed Oct. 17, 2022 Notice of Allowance dated Feb. 15, 2023.
U.S. Appl. No. 17/185,777, filed Feb. 25, 2021 Non-Final Office Action dated Feb. 9, 2022.
U.S. Appl. No. 17/185,777, filed Feb. 25, 2021 Notice of Allowance dated Jun. 10, 2022.
U.S. Appl. No. 17/187,536, filed Feb. 26, 2021 Final Office Action dated Jul. 2, 2024.
U.S. Appl. No. 17/191,551, filed Mar. 3, 2021 Non-Final Office Action dated Aug. 16, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/696,675, filed Mar. 16, 2022 Non-Final Office Action dated Jun. 11, 2024.
U.S. Appl. No. 17/725,394, filed Apr. 20, 2022 Non-Final Office Action dated Jun. 17, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Final Office Action dated Aug. 8, 2024.
U.S. Appl. No. 18/524,620, filed Nov. 30, 2023 Non-Final Office Action dated Jun. 18, 2024.
PCT/US2023/015536 filed Mar. 17, 2023 International Preliminary Report on Patentability dated Sep. 10, 2024.
PCT/US2023/018076 filed Apr. 10, 2023 International Preliminary Report on Patentability dated Oct. 8, 2024.
PCT/US2023/019130 filed Apr. 19, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Notice of Allowance dated Nov. 8, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Notice of Allowance dated Oct. 23, 2024.
U.S. Appl. No. 17/689,773, filed Mar. 8, 2022 Advisory Action dated Nov. 1, 2024.
U.S. Appl. No. 17/725,394, filed Apr. 20, 2022 Non-Final Office Action dated Nov. 19, 2024.

(56) References Cited

OTHER PUBLICATIONS

U.S. Appl. No. 17/849,447, filed Jun. 24, 2022 Advisory Action dated Oct. 24, 2024.
U.S. Appl. No. 17/849,447, filed Jun. 24, 2022 Restriction Requirement dated Apr. 15, 2024.
U.S. Appl. No. 17/863,211, filed Jul. 12, 2022 Restriction Requirement dated Nov. 15, 2024.
U.S. Appl. No. 18/524,620, filed Nov. 30, 2023 Notice of Allowance dated Sep. 12, 2024.
U.S. Appl. No. 17/689,773, filed Mar. 8, 2022 Notice of Allowance dated Jan. 15, 2025.
U.S. Appl. No. 17/696,675, filed Mar. 16, 2022 Final Office Action dated Dec. 5, 2024.
U.S. Appl. No. 18/607,165 filed Mar. 15, 2024 Non-Final Office Action dated Jan. 15, 2025.

* cited by examiner

OPTICAL CONNECTION SYSTEMS AND METHODS THEREOF

PRIORITY

This application is a continuation of U.S. patent application Ser. No. 17/967,794, filed Oct. 17, 2022, now U.S. Pat. No. 11,638,536, which is a continuation of U.S. patent application Ser. No. 17/185,777, filed Feb. 25, 2021, now U.S. Pat. No. 11,474,310, which claims the benefit of priority to U.S. Provisional Application No. 62/983,402, filed Feb. 28, 2020, each of which is incorporated by reference in its entirety into this application.

BACKGROUND

At times, a tip of a peripherally inserted central catheter ("PICC") or central venous catheter ("CVC") can move becoming displaced from an ideal position in a patient's superior vena cava ("SVC"). A clinician believing such a PICC or CVC has displaced typically checks for displacement by chest X-ray and replaces the PICC or CVC if necessary. Because X-rays expose patients to ionizing radiation, medical devices such as PICCs and CVCs are being developed with integrated optical-fiber stylets for clinicians to easily and safely check for displacement thereof. However, in order for the clinicians to check for displacement, the PICCs or CVCs, which are sterile as provided, need to be at least optically connected to non-sterile capital equipment without compromising sterile conditions. Therefore, there is a need for a relay module that allows for single-use medical devices such as the foregoing PICCs and CVCs to be at least optically connected to non-sterile capital equipment without compromising sterile conditions.

Disclosed herein are optical connection systems including electrical-and-optical connection systems and methods thereof.

SUMMARY

Disclosed herein is an electrical-and-optical connection system including, in some embodiments, an extension tube having a plug and a relay module having a receptacle. The extension tube includes one or more optical-fiber cores extending along a length of the extension tube, one or more electrical wires extending along the length of the extension tube over the one or more optical fibers, and the plug. The plug is formed of a metal piece around the one or more electrical wires. The plug is configured to pierce through at least a sterile barrier. The relay module is configured to relay electrical and optical signals to a receiver thereof. The relay module includes one or more optical-fiber cores within a housing of the relay module, one or more electrical wires within the housing of the relay module, and the receptacle disposed in the housing. The receptacle is configured to simultaneously accept insertion of the plug therein and establish both electrical and optical connections between the plug and the receptacle from a sterile field to a non-sterile field.

In some embodiments, the metal piece is fixedly coupled to the one or more electrical wires of the extension tube by an electrically conductive adhesive.

In some embodiments, the metal piece is crimped onto the one or more electrical wires of the extension tube fixedly coupling the metal piece thereto.

In some embodiments, the receptacle includes one or more electrical contacts configured to form the electrical connection with the metal piece when the plug is inserted into the receptacle with the sterile barrier therebetween. Such a configuration enables the electrical connection from the sterile field to the non-sterile field.

In some embodiments, the receptacle includes an optical receiver configured to accept insertion of an optical terminal of the plug and form the optical connection when the plug is inserted into the receptacle with the sterile barrier therebetween. Such a configuration enables the optical connection from the sterile field to the non-sterile field.

In some embodiments, the electrical-and-optical connection system further includes a plug-inserting device configured to removably attach to a surface of the relay module. The plug-inserting device includes a plug holder configured to hold the extension tube or the plug. The plug-inserting device is configured to insert the plug into the receptacle when the plug-inserting device is attached to the relay module, the plug holder is holding the plug, and the plug-inserting device is actuated to insert the plug into the receptacle.

In some embodiments, the plug-inserting device includes a lever as an actuator for inserting the plug into the receptacle. The lever is configured to insert the plug into the receptacle when the lever is moved through a circular sector toward the plug holder.

In some embodiments, the relay module is configured to sit on or alongside a patient beneath the sterile barrier.

In some embodiments, the housing includes a patient-facing surface configured to be adhered to the patient. Such a configuration enables the relay module to be secured to the patient while establishing both the electrical and optical connections between the plug and the relay module.

Also disclosed herein is an optical connection system including, in some embodiments, an extension tube having extension-tube connector and a relay module having a relay-module connector. The extension tube includes one or more optical-fiber cores extending along a length of the extension tube and the extension-tube connector. The extension-tube connector includes an optical terminal disposed in a mating surface of the extension-tube connector. The relay module is configured to relay optical signals to a receiver thereof. The relay module includes one or more optical-fiber cores within a housing of the relay module and the relay-module connector. The relay-module connector includes an optical receiver disposed in a mating surface of the relay-module connector. The extension-tube connector and the relay-module connector are configured to mate across a transparent window of a sterile barrier and establish an optical connection between the optical terminal in a sterile field and the optical receiver in a non-sterile field.

In some embodiments, the extension-tube connector includes one or more alignment magnets disposed in the mating surface of the extension-tube connector around an optical terminal. In addition, the relay-module connector includes one or more alignment magnets disposed in the mating surface of the relay-module connector around an optical receiver.

In some embodiments, a shape of each connector of the extension-tube connector and the relay-module connector enforces a particular orientation of the extension-tube connector and the relay-module connector when mated across the transparent window.

In some embodiments, magnetic poles of the one or more alignment magnets of each connector of the extension-tube connector and the relay-module connector enforces a particular orientation of the extension-tube connector and the relay-module connector when mated across the transparent window.

In some embodiments, a shape of each connector of the extension-tube connector and the relay-module connector is rotationally symmetric. Such a configuration allows a number of rotationally equivalent orientations of the extension-tube connector and the relay-module connector when mated across the transparent window.

In some embodiments, all magnetic poles of the one or more alignment magnets of the extension-tube connector are of a same orientation but opposite all magnetic poles of the one or more alignment magnets of the relay-module connector. Such a configuration allows a number of rotationally equivalent orientations of the extension-tube connector and the relay-module connector when mated across the transparent window.

In some embodiments, the relay module is configured to sit on or alongside a patient beneath the sterile barrier.

In some embodiments, the housing includes a patient-facing surface configured to be adhered to the patient. Such a configuration enables the relay module to be secured to the patient while establishing both the electrical and optical connections between the plug and the relay module.

Also disclosed herein is a method of an electrical-and-optical connection system. The method includes, in some embodiments, a relay-module placing step, a sterile-barrier placing step, and a first plug-inserting step. The relay-module placing step includes placing a relay module on or alongside patient. The sterile-barrier placing step includes placing a sterile barrier over the patient. Such a step establishes a sterile field over the sterile barrier and a non-sterile field under the sterile barrier. The first plug-inserting step includes inserting a plug of an extension tube communicatively connected to a medical device in the sterile field into a receptacle of the relay module in the non-sterile field. The first plug-inserting step simultaneously establishes both electrical and optical connections between the medical device and the relay module across the sterile barrier.

In some embodiments, the relay-module placing step occurs before the sterile-barrier placing step.

In some embodiments, the method further includes a mounting step and second plug-inserting step. The mounting step includes mounting a plug-inserting device over a surface of the relay module. The second plug-inserting step includes inserting the plug into a plug holder of the plug-inserting device.

In some embodiments, the method further includes an actuating step of actuating a lever of the plug-inserting device for inserting the plug into the receptacle.

Also disclosed herein is a method of an optical connection system. The method includes, in some embodiments, a relay-module placing step, a sterile-barrier placing step, and a mating step. The relay-module placing step includes placing a relay module on or alongside a patient. The sterile-barrier placing step includes placing a sterile barrier having a transparent window over the patient. Such a step establishes a sterile field over the sterile barrier and a non-sterile field under the sterile barrier. The mating step includes mating an extension-tube connector of an extension tube communicatively connected to a medical device in the sterile field with a relay-module connector of the relay module in the non-sterile field with the transparent window between the extension-tube connector and the relay-module connector. The mating step establishes the optical connection between the medical device and the relay module across the sterile barrier.

In some embodiments, the relay-module placing step occurs before the sterile-barrier placing step.

In some embodiments, the mating step includes orientating the extension-tube connector such that its shape matches a shape of the relay-module connector.

In some embodiments, the mating step includes orientating the extension-tube connector such that magnetic poles of its one or more alignment magnets complement magnetic poles of one or more alignment magnets of the relay-module connector.

These and other features of the concepts provided herein will become more apparent to those of skill in the art in view of the accompanying drawings and following description, which describe particular embodiments of such concepts in greater detail.

DRAWINGS

DESCRIPTION

Figure 1:
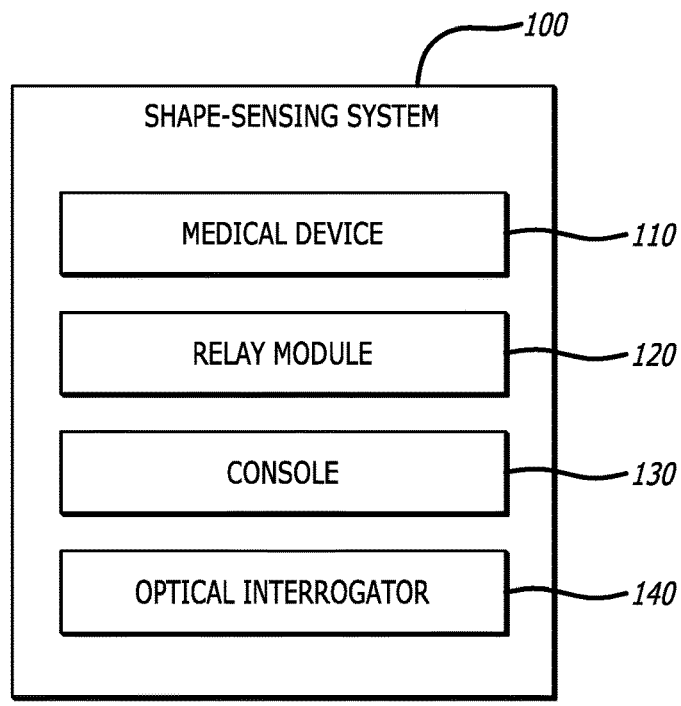
FIG. 1 is a block diagram of a first shape-sensing system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need for a relay module that allows for single-use medical devices such as the foregoing PICCs and CVCs to be at least optically connected to non-sterile capital equipment without compromising sterile conditions. Disclosed herein are optical connection systems including electrical-and-optical connection systems and methods thereof.

Features of the optical connection systems provided herein will become more apparent with reference to the accompanying drawings and the following description, which provide particular embodiments of the optical connection systems in greater detail. For context, shape-sensing systems are described first followed by medical devices and relay modules of the shape-sensing systems, as well as methods of the foregoing. The optical connection systems and the electrical-and-optical connection systems are described among a combination of the shape-sensing systems, the medical devices, and the relay modules.

Shape-Sensing Systems

Figure 2:
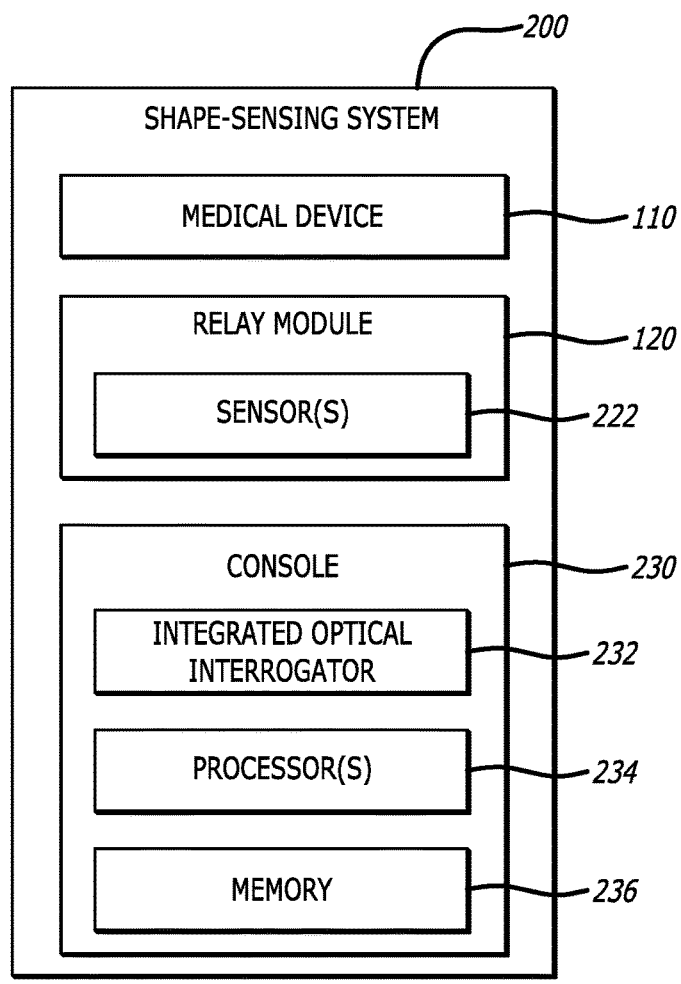
FIG. 2 is a block diagram of a second shape-sensing system in accordance with some embodiments.
Figure 3:
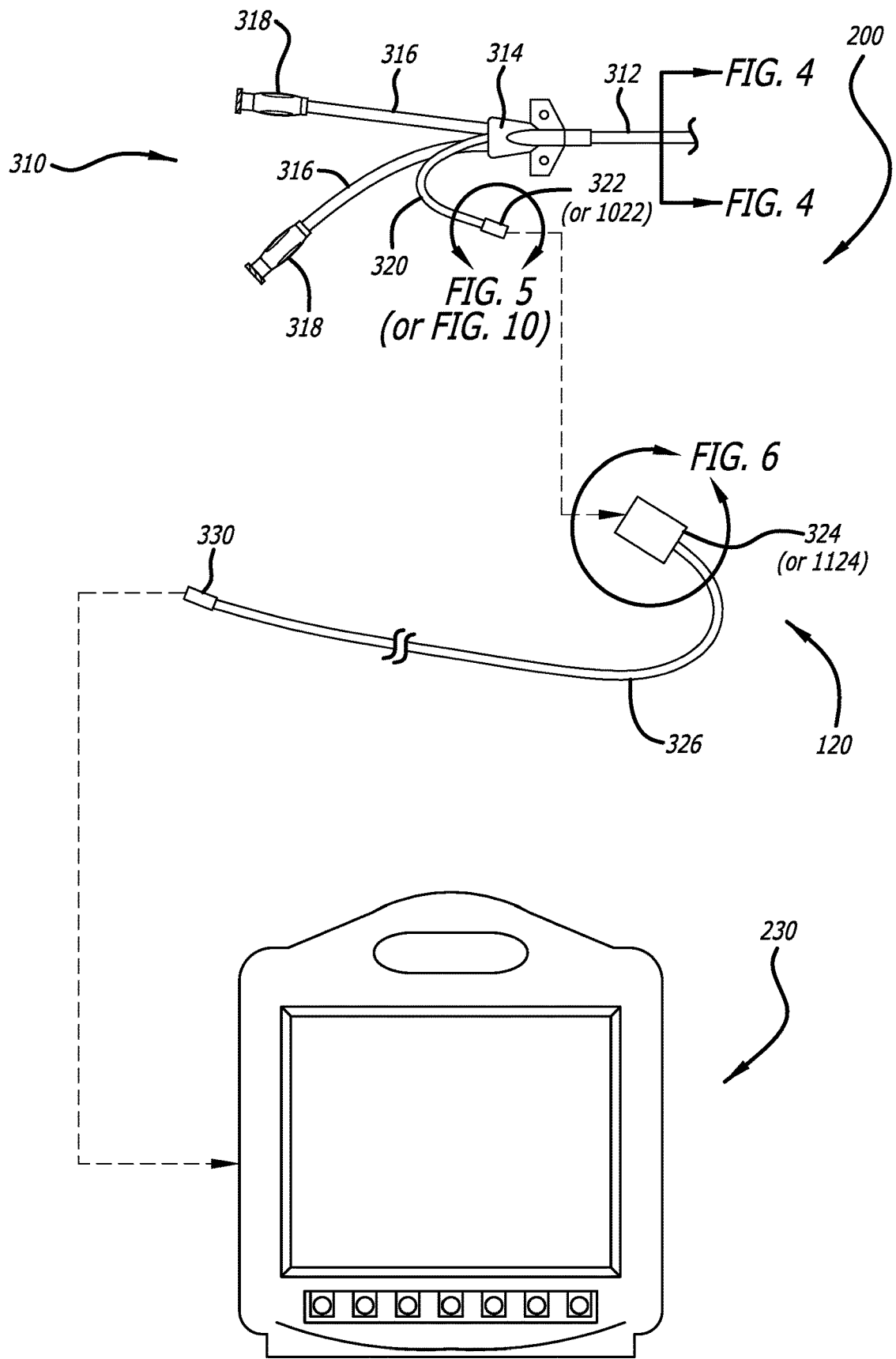
FIG. 3 illustrates the second shape-sensing system in accordance with some embodiments.
Figure 8:
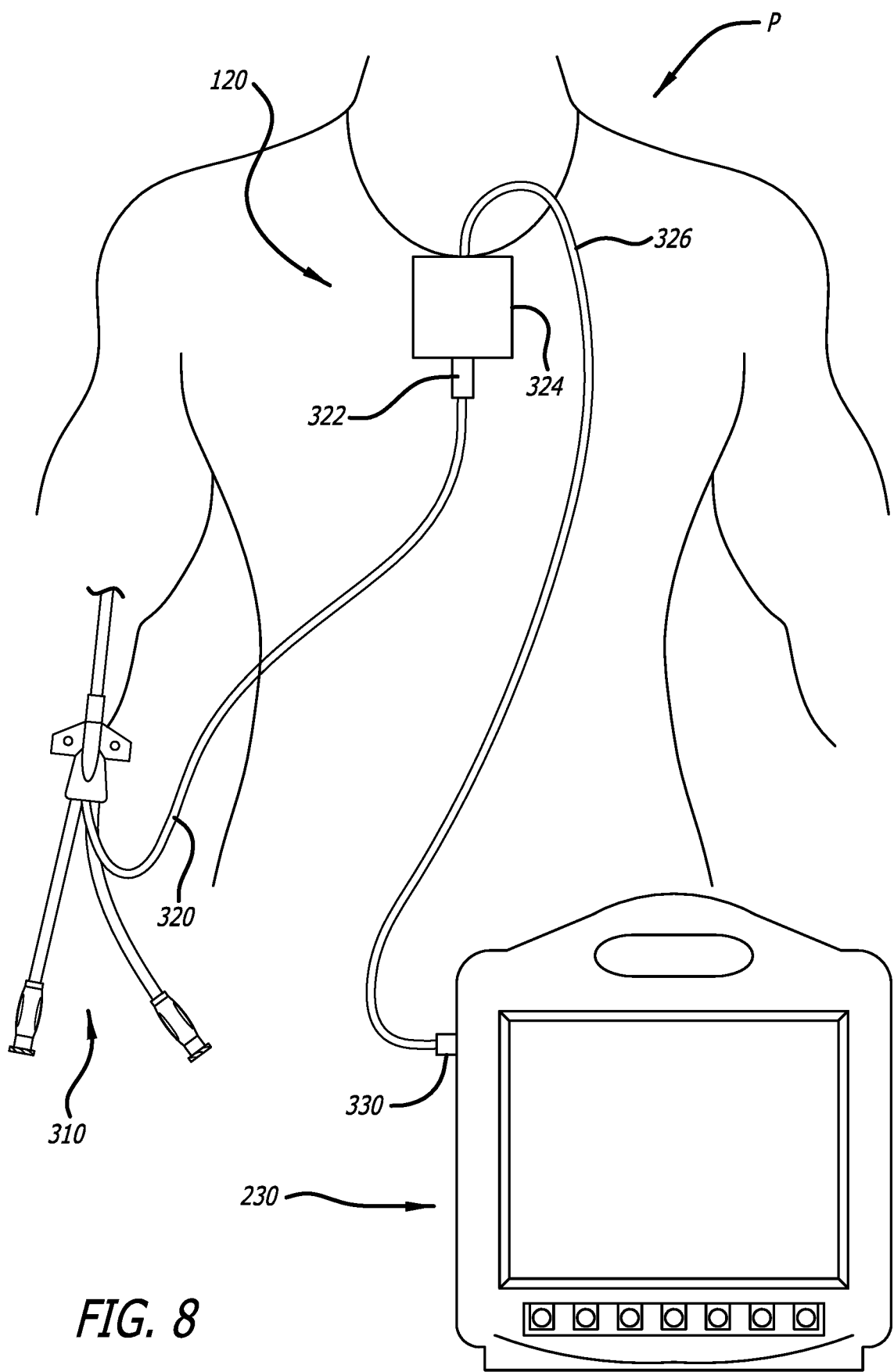
FIG. 8 illustrates the second shape-sensing system in use during a patient procedure in accordance with some embodiments.
Figure 9:
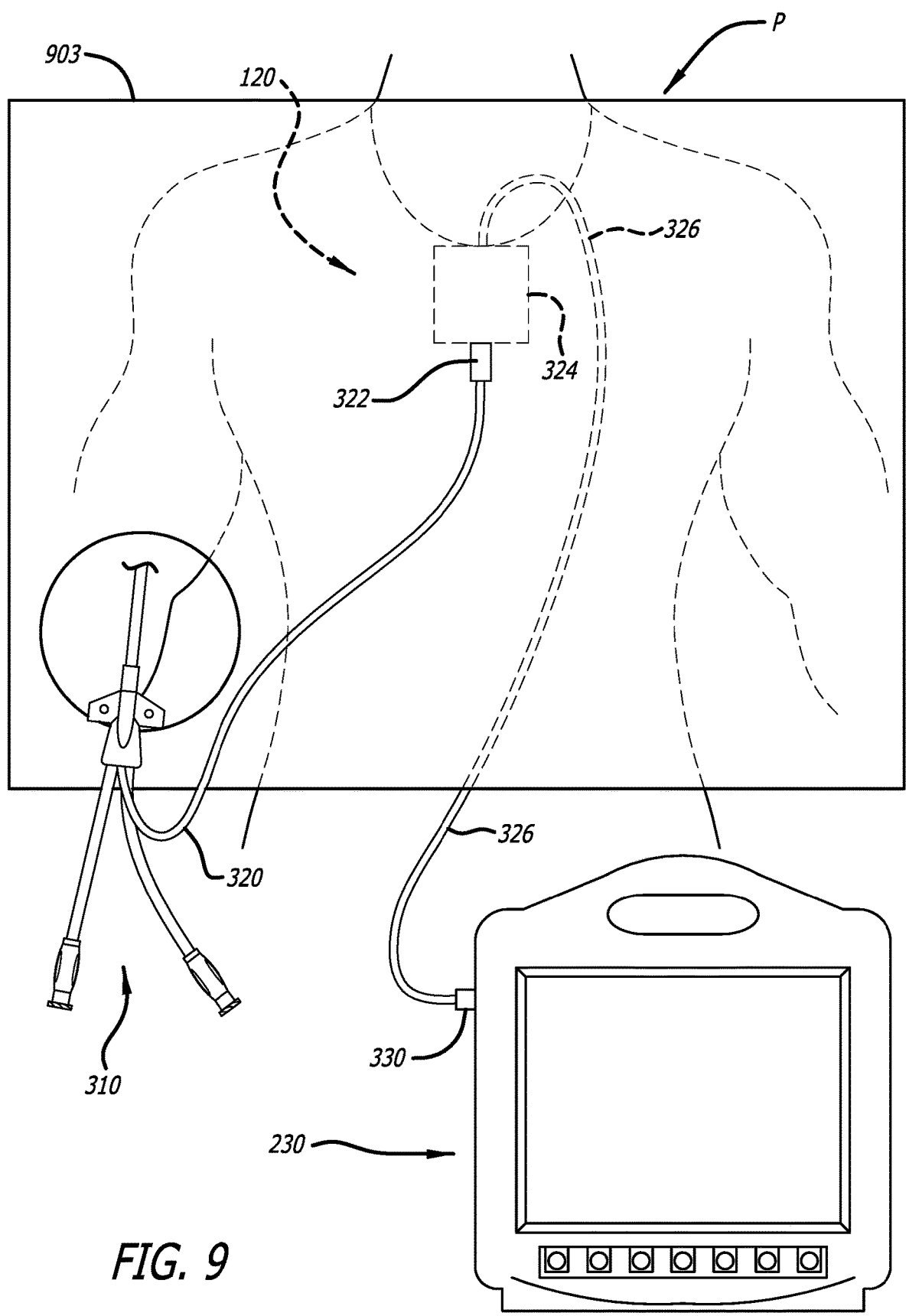
FIG. 9 illustrates the second shape-sensing system in use during a patient procedure with a sterile barrier in accordance with some embodiments.

FIG. 1 is a block diagram of a first shape-sensing system 100 in accordance with some embodiments. FIG. 2 is a block diagram of a second shape-sensing system 200 in accordance with some embodiments. FIG. 3 illustrates the second shape-sensing system 200 in accordance with some embodiments. FIG. 8 illustrates the second shape-sensing system 200 in use during a patient procedure in accordance with some embodiments. FIG. 9 illustrates the second shape-sensing system 200 in use during a patient procedure with a sterile barrier 903 in accordance with some embodiments.

As shown, the shape-sensing system 100 or 200 includes, in some embodiments, a medical device 110, a console 130 or 230, and relay module 120 configured for connecting the medical device 110 to a remainder of the shape-sensing system 100 or 200 such as the console 230. The medical device 110 is typically used in a sterile field while the relay module 120 and the console 130 or 230 are typically used in a non-sterile field as defined by at least the sterile barrier 903 (e.g., drape) as one of several possible sterile barriers (e.g., drape, plastic holder, sheath, etc.).

The medical device 110 includes at least an integrated optical-fiber stylet including one or more optical-fiber cores, each core, in turn, having a number of fiber Bragg grating ("FBG") sensors along a length thereof for shape sensing with the shape-sensing system 100 or 200. (See integrated optical-fiber stylet 424 in FIG. 4 for an example of the optical-fiber stylet of the medical device 110.) However, the medical device 110 can also include electrical componentry such as an electrocardiogram ("ECG") stylet and one or more electrical wires in support of the ECG stylet.

Certain features of the medical device 110 are set forth in more detail below with respect to particular embodiments of the medical device 110 such as the PICC 310. That said, some features (e.g., the optical fiber stylet, the ECG stylet, etc.) set forth below with respect to one or more embodiments of the medical device 110 such as the PICC 310 can be shared among two or more embodiments of the medical device 110. As such, "medical device 110" is used herein to generically refer to more than one embodiment of the medical device 110 when needed for expository expediency. This is despite certain features having been described with respect to particular embodiments of the medical device 110 such as the PICC 310.

While only shown for the console 230, each console of the consoles 130 and 230 includes memory 236 and one or more processors 234 for converting reflected optical signals from the optical-fiber stylet of the medical device 110 into displayable shapes for the medical device 110. The displayable shapes for the medical device 110 can be displayed on an integrated display screen integrated into the console 130 or 230 or a display screen of a stand-alone monitor coupled to the console 130 or 230.

The shape-sensing system 100 further includes a stand-alone optical interrogator 140 communicatively coupled to the console 130, whereas the shape-sensing system 200 further includes an integrated optical interrogator 232 integrated into the console 230. The optical interrogator 140 or 232 is configured to send input optical signals into the optical-fiber stylet of the medical device 110 by way of the relay module 120 and receive reflected optical signals from the optical-fiber stylet by way of the relay module 120.

The relay module 120 includes a housing 324, a cable 326 extending from the housing 324, and one or more optical-fiber cores 628 ("optical fiber 628") extending through the housing 324 and along the cable 326. (For the optical fiber 628, see FIG. 6.) The relay module 120 is configured to establish at least an optical connection between the optical-fiber stylet of the medical device 110 and the optical fiber 628 of the relay module 120. The relay module 120 is also configured with a plug 330 at a terminus of the cable 326 to establish at least another optical connection between the optical fiber 628 of the relay module 120 and the optical interrogator 140 or 232. The optical fiber 628 of the relay module 120 is configured to convey the input optical signals from the optical interrogator 140 or 232 to the optical-fiber stylet of the medical device 110 and the reflected optical signals from the optical-fiber stylet to the optical interrogator 140 or 232.

The relay module 120 can also be configured to establish an electrical connection between the medical device 110 and the relay module 120, an electrical connection between the relay module 120 and the console 103 or 230, or both as set forth in more detail below. In support of such electrical connections, the relay module 120 can include one or more electricals wires extending through the housing 324 and along the cable 326 like the optical fiber 628.

The relay module 120 can further include one or more sensors 222 selected from at least a gyroscope, an accelerometer, and a magnetometer disposed within the housing 324. The one or more sensors 222 are configured to provide sensor data to the console 130 or 230 by way of the one or more electrical wires within the housing 324 and the cable 326 for determining a reference plane for shape sensing with the optical-fiber stylet of the medical device 110.

Certain features of the relay module 120 are set forth in more detail below with respect to particular embodiments of the relay module 120. That said, some features set forth below with respect to one or more embodiments of the relay module 120 are shared among two or more embodiments of the relay module 120. As such, "relay module 120" is used herein to generically refer to more than one embodiment of the relay module 120 when needed for expository expediency. This is despite certain features having been described with respect to particular embodiments of the relay module 120.

Medical Devices

Figure 4:
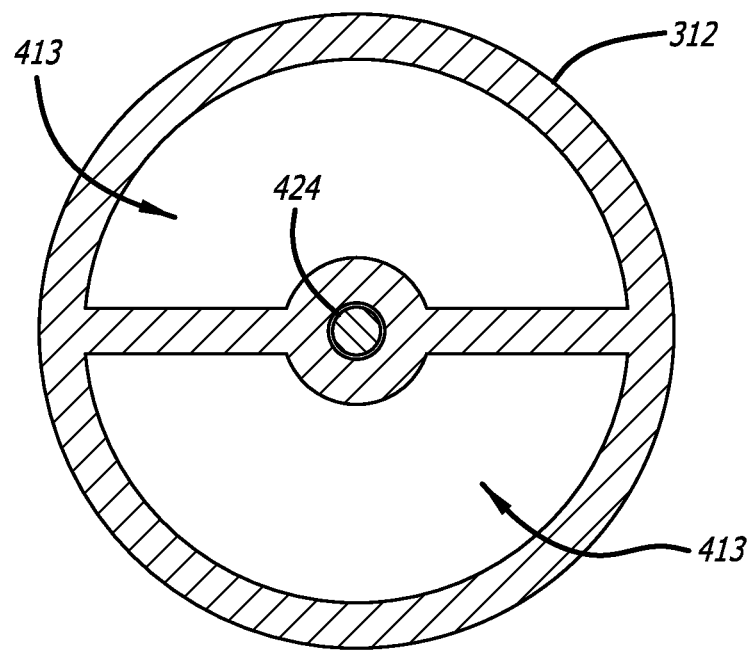
FIG. 4 illustrates a cross-section of a catheter tube of a medical device in accordance with some embodiments.
Figure 5:
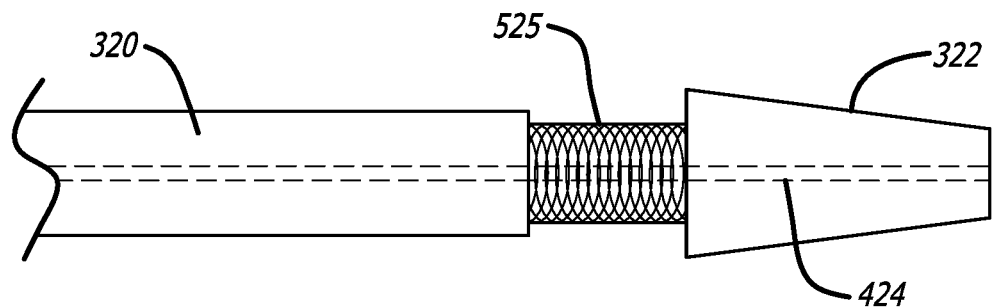
FIG. 5 illustrates a plug of an extension tube of a medical device for establishing both optical and electrical connections in accordance with some embodiments.

FIG. 3 also illustrates a PICC 310 as the medical device 110 in accordance with some embodiments. FIG. 4 illustrates a cross-section of a catheter tube 312 of the PICC 310 including an integrated optical-fiber stylet 424 in accordance with some embodiments. FIG. 5 illustrates a plug 322 of an extension tube or cable 320 of the medical device 110 for establishing both optical and electrical connections in accordance with some embodiments.

As shown, the PICC 310 includes the catheter tube 312, a bifurcated hub 314, two extension legs 316, and two Luer connectors 318 operably connected in the foregoing order. The catheter tube 312 includes two catheter-tube lumens 413 and the optical-fiber stylet 424 disposed in a longitudinal bead of the catheter tube 312 such as between the two catheter-tube lumens 413, as extruded. Optionally, in a same or different longitudinal bead of the catheter tube 312, the PICC 310 can further include the ECG stylet. The bifurcated hub 314 has two hub lumens correspondingly fluidly connected to the two catheter-tube lumens 413. Each extension leg of the two extension legs 316 has an extension-leg lumen fluidly connected to a hub lumen of the two hub lumens. The PICC 310 further includes the extension tube 320 either extending from the bifurcated hub 314 or communicatively coupled to the bifurcated hub 314. When extending from the bifurcated hub 314, the extension tube 320 can be a skived portion of the catheter tube 312 including the optical-fiber stylet 424 and, if present, the ECG stylet, which extension tube 320 can terminate in the plug 322 for establishing an optical connection between the optical-fiber stylet 424 of the PICC 310 and the optical fiber 628 of the relay module 120, as well as any electrical connections. The skived portion of the catheter tube 312 can be disposed in another tube, which, in combination, forms the extension tube 320 terminating in the plug 322 for establishing the foregoing optical and electrical connections.

While the PICC 310 is provided as a particular embodiment of the medical device 110 of the shape-sensing system 100 or 200, it should be understood that any of a number of medical devices including catheters such as a CVC can include at least an optical-fiber stylet and, optionally, electrical componentry such as the ECG stylet and the one or more wires in support thereof, terminating in a plug for establishing an optical connection or both optical and electrical connections between the medical device and the relay module 120.

Relay Modules

Figure 6:
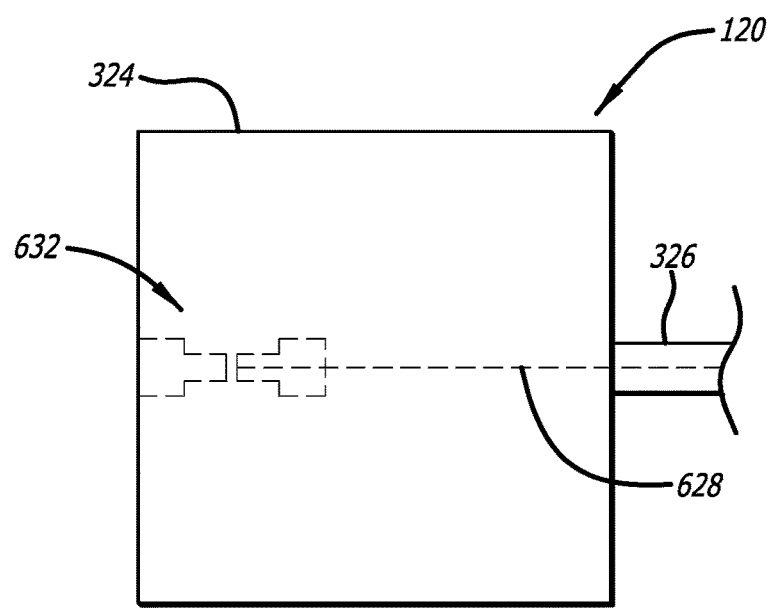
FIG. 6 illustrates a detailed view of a relay module with a receptacle for establishing optical connections or both optical and electrical connections in accordance with some embodiments.

FIG. 6 illustrates a detailed view of the relay module 120 with a receptacle 632 for establishing optical connections or both optical and electrical connections in accordance with some embodiments. FIG. 9 illustrates the second shape-sensing system 200 in use during a patient procedure with the sterile barrier 903 in accordance with some embodiments.

As shown, the relay module 120 includes the housing 324, the receptacle 632 disposed in the housing 324, the cable 326 extending from the housing 324, and at least the optical fiber 628 within the housing 324 and the cable 326. Again, the relay module 120 can include one or more electricals wires extending through the housing 324 and along the cable 326 similar to the optical fiber 628 in some embodiments.

The receptacle 632 includes an optical receiver configured to accept insertion of an optical terminal of a plug of the medical device 110 (e.g., the plug 322 of the PICC 310) for establishing an optical connection between the relay module 120 and the optical-fiber stylet of the medical device 110 (e.g., the optical-fiber stylet 424 of the PICC 310) when the plug is inserted into the receptacle 632. The receptacle 632 can also include one or more electrical contacts configured to contact an electrical terminal (e.g., the metal piece of the plug 322) of the plug of the medical device 110 (e.g., the plug 322 of the PICC 310), when present, for establishing an electrical connection between the relay module 120 and the one or more electrical wires of the medical device 110 when the plug is inserted into the receptacle 632.

The cable 326 includes the plug 330 for establishing an optical connection between the relay module 120 and the optical interrogator 232 of the console 230, as well as an electrical connection between the relay module 120 and the console 230 in some embodiments.

The optical fiber 628 extends from the receptacle 632 through the cable 326 to the plug 330. The optical fiber 628 is configured to convey the input optical signals from the optical interrogator 232 to the optical-fiber stylet of the medical device 110 (e.g., the optical-fiber stylet 424 of the PICC 310) and the reflected optical signals from the optical-fiber stylet to the optical interrogator 232.

As set forth above, the relay module 120 can further include the one or more sensors 222 selected from the gyroscope, the accelerometer, and the magnetometer disposed within the housing 324. The one or more sensors 222 are configured to provide sensor data for determining a reference plane for shape sensing with the optical-fiber stylet of the medical device 110 (e.g., the optical-fiber stylet 424 of the PICC 310).

As with the optical fiber 628, the one or more electrical wires, when present in the relay module 120, extend from the one or more sensors 222, if present, the receptacle 632, or both the one or more sensors 222 and the receptacle 632 through the cable 326 to the plug 330. In addition to any needed electrical power, the one or more electrical wires are configured to convey input electrical signals from the console 230 to the one or more sensors 222, when present in the relay module 120. The one or more electrical wire are also configured to convey any output electrical signals from the one or more sensors 222, the ECG stylet, if present in the medical device 110, or both the one or more sensors 222 and the ECG stylet to the console 230.

The relay module 120 is configured to sit beneath the sterile barrier 903 on or alongside a patient P such as on a chest of the patient. As such, the relay module 120 need not require disinfection or sterilization. However, should the relay module 120 require disinfection or sterilization, the relay module 120 can be configured to be amenable to disinfection or sterilization. For example, the housing 324 of the relay module 120 can be non-porous or chemically resistant to oxidants. The relay module 120 can be configured for manual disinfection with a ChloraPrepR product by Becton, Dickinson and Company (Franklin Lakes, NJ), or the relay module 120 can be configured for automatic high-level disinfection or sterilization with vaporized $H_2O_2$ by way of Trophon® by Nanosonics Inc. (Indianapolis, IN).

While not shown, the housing 324 of the relay module 120 can include a loop extending from the housing 324, a tether point integrated into the housing 324, or a ball-lock-pin receiver integrated into the housing 324 configured for attaching a neck strap to the relay module 120. The loop, the tether point, or the ball-lock-pin receiver enables the relay module 120 to be secured to a neck of the patient P while sitting on the patient's chest. Additionally or alternatively, the housing 324 includes a patient-facing surface (e.g., a back of the relay module 120) configured to be adhered to the patient's chest. The patient-facing surface enables the relay module 120 to be secured to the patient while sitting on or alongside the patient whether or not the relay module 120 is also secured to the patient's neck.

Again, the receptacle 632 includes the optical receiver configured to accept insertion of the optical terminal of the plug of the medical device 110 (e.g., the plug 322 of the PICC 310) and form an optical connection when the plug is inserted into the receptacle 632. The receptacle 632 can also include one or more electrical contacts configured to contact the electrical terminal (e.g., the metal piece of the plug 322) of the plug of the medical device 110 (e.g., the plug 322 of the PICC 310), when present, for establishing an electrical connection between the relay module 120 and the one or more electrical wires of the medical device 110 when the plug is inserted into the receptacle 632. However, with the relay module 120, such optical and electrical connections are formed with the sterile barrier 903 between the relay module 120 and the medical device 110. The receptacle 632 and the plug of the medical device 110 enable such connections from a sterile field (e.g., above the sterile barrier 903) including the medical device 110 such as the PICC 310 to a non-sterile field (e.g., beneath the sterile barrier 903) including the relay module 120.

Connection Systems

FIG. 5 illustrates the plug 322 of the extension tube 320 of the medical device 110 for establishing both optical and electrical connections in accordance with some embodiments. FIG. 6 illustrates a detailed view of the relay module 120 with the receptacle 632 for establishing optical connections or both optical and electrical connections in accordance with some embodiments.

As shown, an electrical-and-optical connection system can include the extension tube 320 having the plug 322 and the relay module 120 having the receptacle 632.

As set forth above, the extension tube 320 can include one or more optical-fiber cores extending from the optical-fiber stylet 424 along a length of the extension tube 320, one or more electrical wires (e.g., one or more electrical wires 525) extending along the length of the extension tube 320 over the one or more optical fibers such as braided over the one or more optical fibers, and the plug 322.

The plug 322 is formed of a metal piece (e.g., a metal ferrule) around the one or more electrical wires, which, in turn, are over the one or more optical-fiber cores. The metal piece can be fixedly coupled to the one or more electrical wires of the extension tube 320 by an electrically conductive adhesive (e.g., electrically conductive epoxy), crimped onto the one or more electrical wires of the extension tube 320, or a combination thereof. The plug 322 or the metal piece thereof is sufficiently tapered such that it is configured to pierce through at least a sterile barrier such as the sterile barrier 903.

As set forth above, the relay module 120 can be configured to relay both optical signals and electrical signals to a receiver thereof such as the console 230 of the shape-sensing system 200. When so configured, the relay module 120 includes one or more optical-fiber cores within the housing 324 of the relay module 120, one or more electrical wires within the housing 324, and the receptacle 632 disposed in the housing 324.

The receptacle 632 is configured to simultaneously accept insertion of the plug 322 therein and establish both electrical and optical connections between the plug 322 and the receptacle 632 from a sterile field to a non-sterile field. For the optical connection, the receptacle 632 includes the optical receiver set forth above configured to accept insertion of the optical terminal of the plug 322 and form the optical connection when the plug 322 is inserted into the receptacle 632 with the sterile barrier 903 therebetween. Such a configuration enables the optical connection from the sterile field to the non-sterile field. For the electrical connection, the receptacle 632 includes the one or more electrical contacts set forth herein configured to form the electrical connection with the metal piece when the plug 322 is inserted into the receptacle 632 with the sterile barrier 903 therebetween. Such a configuration enables the electrical connection from the sterile field to the non-sterile field.

Figure 7:
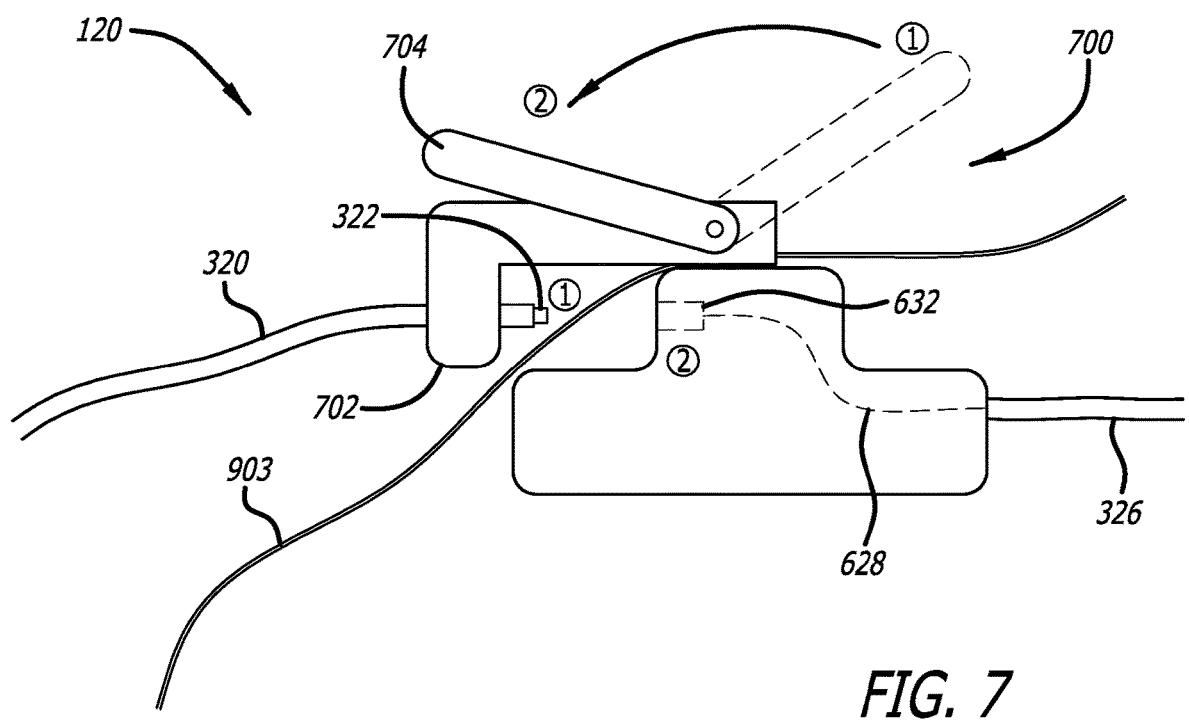
FIG. 7 illustrates a plug-inserting device in accordance with some embodiments.

FIG. 7 illustrates a plug-inserting device 700 in accordance with some embodiments.

As shown, the electrical-and-optical connection system set forth above can further include the plug-inserting device 700. The plug-inserting device 700 is configured to removably attach to a surface of the relay module 120 with the sterile barrier 903 between the plug-inserting device 700 and the relay module 120 as shown in FIG. 7 for inserting the plug 322 into the receptacle 632 of the relay module 120.

The plug-inserting device 700 includes a plug holder 702 and a lever 704. The plug holder 702 is configured to hold the extension tube 320 or the plug 322. The lever 704 is an actuator configured to insert the plug 322 into the receptacle 632 of the relay module 120 when the lever 704 is moved through a circular sector toward the plug holder 702 as shown in FIG. 7. Indeed, the plug-inserting device 700 is configured to insert the plug 322 into the receptacle 632 when the plug-inserting device 700 is attached to the relay module 120, the plug holder 702 is holding the plug 322, and the plug-inserting device 700 is actuated by the lever 704 to insert the plug 322 into the receptacle 632.

Figure 10:
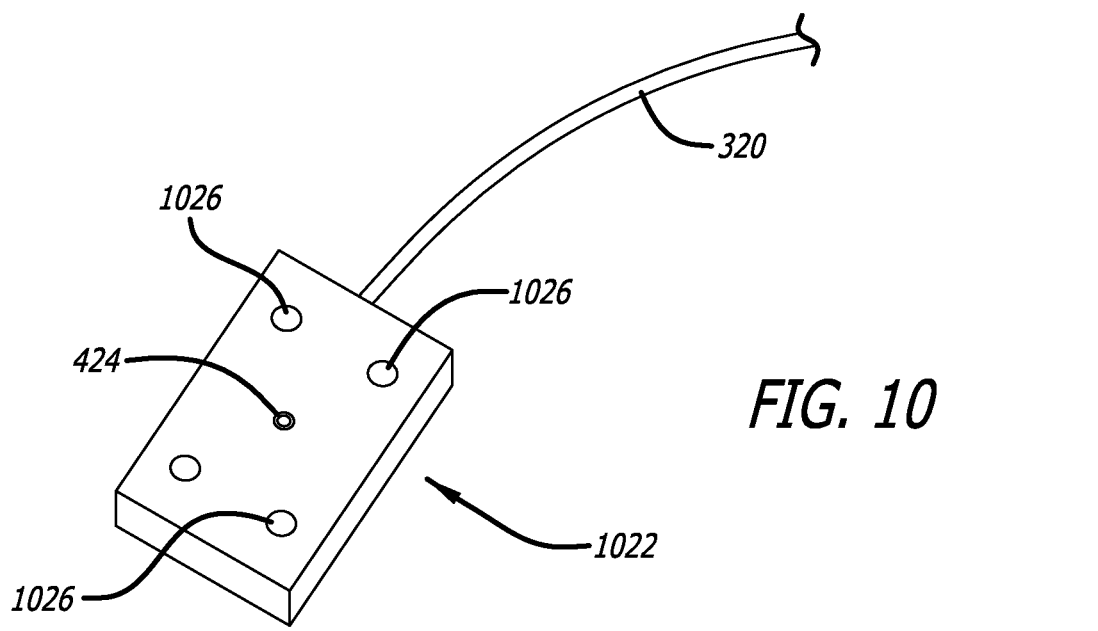
FIG. 10 illustrates an extension-tube optical connector of an extension tube of a medical device in accordance with some embodiments.
Figure 11:
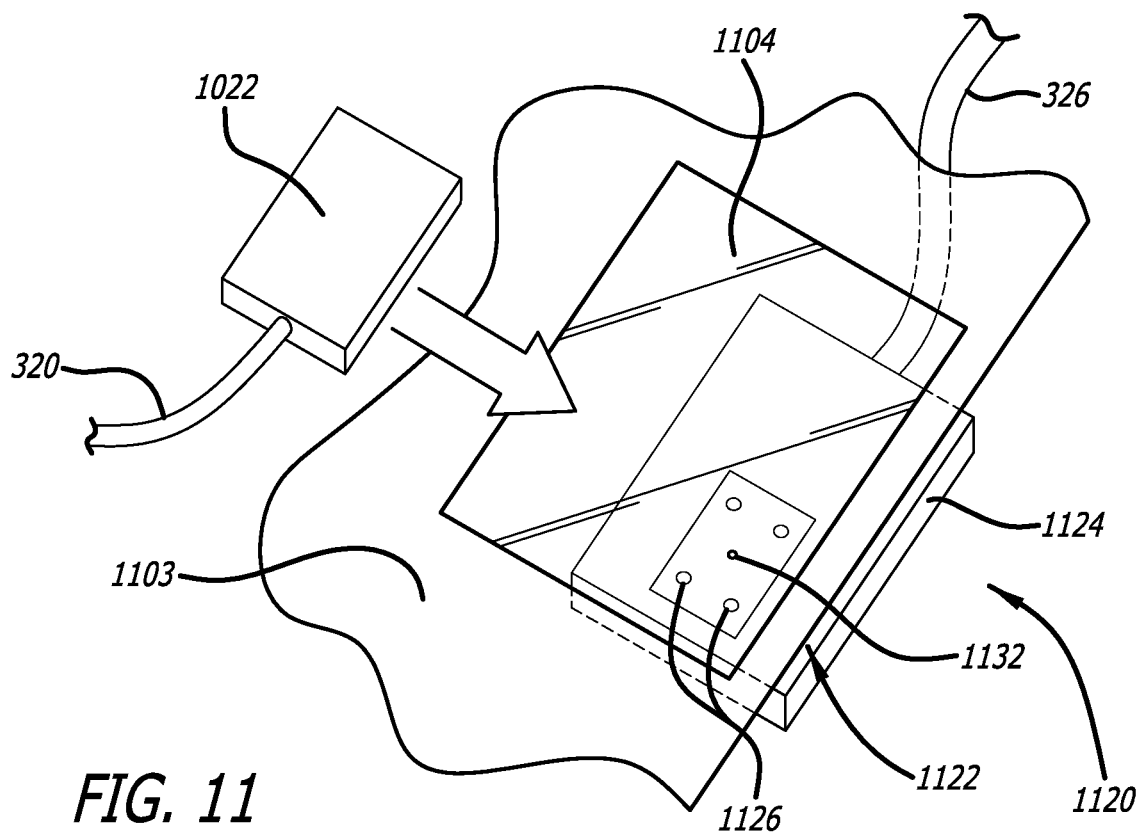
FIG. 11 illustrates a relay module with a relay-module optical connector for establishing optical connections in accordance with some embodiments.

FIG. 10 illustrates an extension-tube optical connector 1022 of the extension tube 320 of the medical device 110 in accordance with some embodiments. FIG. 11 illustrates a relay module 1120 with a relay-module optical connector 1122 for establishing optical connections across a sterile barrier 1103 in accordance with some embodiments.

As shown, an optical connection system can include the extension tube 320 having the extension-tube connector 1022 and the relay module 1120 having the relay-module connector 1122.

As set forth above, the extension tube 320 can include one or more optical-fiber cores extending from the optical-fiber stylet 424 along a length of the extension tube 320. The one or more optical-fibers can extend to an optical terminal in a mating surface of the extension-tube connector 1022.

The extension-tube connector 1022 includes one or more alignment magnets 1026 disposed in the mating surface of the extension-tube connector 1022 around the optical terminal or an end portion of the optical-fiber stylet 424.

As set forth above, the relay module 120 can be configured to relay optical signals to a receiver thereof such as the console 230 of the shape-sensing system 200. When the relay module 1120 is so configured, the relay module 1120 includes one or more optical-fiber cores within a housing 1124 of the relay module 1120 and the relay-module connector 1122.

The relay-module connector 1122 includes one or more alignment magnets 1126 disposed in a mating surface of the relay-module connector 1122 around an optical receiver 1132.

The extension-tube connector 1022 and the relay-module connector 1122 are configured to mate across a transparent window 1104 of the sterile barrier 1103 (e.g., drape) and establish an optical connection between the optical terminal of the extension-tube connector 1022 in a sterile field and the optical receiver of the relay-module connector 1122 in a non-sterile field.

A shape of each connector of the extension-tube connector 1022 and the relay-module connector 1122 can be configured to enforce a particular orientation of the extension-tube connector 1022 and the relay-module connector 1122 when mated across the transparent window 1104 of the sterile barrier 1103. For example, each connector of the extension-tube connector 1022 and the relay-module connector 1122 shown in FIG. 11 is rectangular or longer than it is wide, thereby enforcing two of the four most reasonable orientations for rectangular connectors.

Magnetic poles of the one or more alignment magnets 1026 and 1126 of each connector of the extension-tube connector 1022 and the relay-module connector 1122 can additionally or alternatively be configured to enforce a particular orientation of the extension-tube connector 1022 and the relay-module connector 1122 when mated across the transparent window 1104 of the sterile barrier 1103. For example, a first side of the extension-tube connector 1022 can include a first pair of the alignment magnets 1026 having a same magnetic pole orientation (e.g., N). A second side of the extension-tube connector 1022 can include a second pair of the alignment magnets 1026 having a same magnetic pole orientation (e.g., S) but different than the first side of the extension-tube connector. The relay-module connector 1122 can be likewise configured such that similar sides of the extension-tube connector 1022 and the relay-module connector 1122 repel each other when brought close to each other and dissimilar sides of the extension-tube connector 1022 and the relay-module connector 1122 attract each other when brought close to each other. In this way, two of the four most reasonable orientations of, for example, square-shaped connectors can be enforced. However, if the extension-tube connector 1022 and the relay-module connector 1122 are rectangular as shown in FIG. 11, both the shape and the magnetic poles configured as in the example can enforce a single orientation.

Notwithstanding the foregoing, a shape of each connector of the extension-tube connector 1022 and the relay-module connector 1122 can be rotationally symmetric. Such a configuration allows a number of rotationally equivalent orientations of the extension-tube connector 102 and the relay-module connector 1122 when mated across the transparent window 1104 of the sterile barrier 1103. For example, all the magnetic poles of the one or more alignment magnets 1026 of the extension-tube connector 1022 can be of a same magnetic pole orientation but opposite all the magnetic poles of the one or more alignment magnets 1126 of the relay-module connector 1122 to complement all the magnetic poles of the one or more alignment magnets 1126 of the relay-module connector 1122. Indeed, such a configuration allows a number of rotationally equivalent orientations of the extension-tube connector 1022 and the relay-module connector 1122 when mated across the transparent window 1104 of the sterile barrier 1103.

Methods

FIG. 9 illustrates the second shape-sensing system 200 in use during a patient procedure with the sterile barrier 903 in accordance with some embodiments.

A method of an electrical-and-optical connection system can be a part of a method of the shape-sensing system 100 or 200. Such a method can include a relay-module placing step, a sterile-barrier placing step, and a first plug-inserting step.

The relay-module placing step includes placing the relay module 1120 on or alongside the patient P such as on the chest of the patient. Prior to the relay-module placing step, the method can further include a disinfecting or sterilizing step of disinfecting or sterilizing the relay module 1120 before placing the relay module 1120 on or alongside the patient.

The sterile-barrier placing step includes placing the sterile barrier 903 over the patient. Such a step establishes a sterile field over the sterile barrier 903 and a non-sterile field under the sterile barrier 903 and can occur after the relay-module placing step.

The first plug-inserting step includes inserting the plug 322 of the extension tube 320 communicatively connected to the medical device 110 (e.g., the PICC 310) in the sterile field into the receptacle 632 of the relay module 120 in the non-sterile field. The first plug-inserting step simultaneously establishes both electrical and optical connections between the medical device 110 (e.g. the PICC 310) and the relay module 120 across the sterile barrier 903.

Before the first plug-inserting step, the method can further include a mounting step and second plug-inserting step. The mounting step includes mounting the plug-inserting device 700 over the surface of the relay module 120. The second plug-inserting step includes inserting the plug 322 into the plug holder 702 of the plug-inserting device 700 for the first plug-inserting step.

Following on the mounting and second plug-inserting steps, the method can further include an actuating step of actuating the lever 704 of the plug-inserting device 700 for inserting the plug 322 into the receptacle 632 during the first plug-inserting step.

A method of an optical connection system can also be a part of a method of the shape-sensing system 100 or 200. Such a method can include a relay-module placing step, a sterile-barrier placing step, and a mating step.

The relay-module placing step includes placing the relay module 1120 on or alongside the patient P such as on the chest of the patient. Prior to the relay-module placing step, the method can further include a disinfecting or sterilizing step of disinfecting or sterilizing the relay module 1120 before placing the relay module 1120 on or alongside the patient.

The sterile-barrier placing step includes placing the sterile barrier 1103 having the transparent window 1104 over the patient. Such a step establishes a sterile field over the sterile barrier 1103 and a non-sterile field under the sterile barrier 1103 and can occur after the relay-module placing step.

The mating step includes mating the extension-tube connector 1022 of the extension tube 320 communicatively connected to the medical device 110 (e.g., the PICC 310) in the sterile field with the relay-module connector 1122 of the relay module 1120 in the non-sterile field with the transparent window 1104 between the extension-tube connector 1022 and the relay-module connector 1122. The mating step establishes the optical connection between the medical device 110 and the relay module 1120 across the sterile barrier 1103.

The mating step includes orientating the extension-tube connector 1022 such that its shape matches the shape of the relay-module connector 1122. The mating step can also include orientating the extension-tube connector 1022 such that the magnetic poles of the one or more alignment magnets 1026 complement the magnetic poles of the one or more alignment magnets 1126 of the relay-module connector 1122.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of an electrical-and-optical connection system, comprising:
    placing a relay module on or alongside a patient, the relay module comprising:
        one or more optical-fiber cores within a housing of the relay module;
        one or more electrical wires within the housing of the relay module; and
        a receptacle disposed in the housing;
    placing a sterile barrier over the patient, thereby establishing a sterile field over the sterile barrier and a non-sterile field under the sterile barrier; and
    inserting a plug of a medical device in the sterile field into the receptacle of the relay module in the non-sterile field, the inserting piercing the sterile barrier and simultaneously establishing both electrical and optical connections between the medical device and the relay module across the sterile barrier.

2. The method according to claim 1, wherein the medical device includes an extension tube, and wherein the plug is connected to the extension tube.

3. The method according to claim 1, further comprising:
    mounting a plug-inserting device over a surface of the relay module; and
    inserting the plug into a plug holder of the plug-inserting device.

4. The method according to claim 3, further comprising actuating a lever of the plug-inserting device for inserting the plug into the receptacle.

5. The method according to claim 1, wherein placing the relay module on or alongside the patient occurs before placing the sterile barrier over the patient.

6. A method of an electrical-and-optical connection system, comprising:
    placing a relay module on or alongside a patient, the relay module comprising:
        one or more optical-fiber cores within a housing of the relay module;
        one or more electrical wires within the housing of the relay module; and
        a relay module connector including an optical receiver disposed in a mating surface, wherein one or more alignment magnets are disposed in the mating surface around the optical receiver;
    placing a sterile drape over the patient, thereby establishing a sterile field over the sterile drape and a non-sterile field under the sterile drape; and
    mating a medical device connector in the sterile field with the relay module connector with the sterile drape therebetween by orienting one or more alignment magnets of the medical device connector with the one or more alignment magnets in the mating surface of the relay module connector such that magnetic poles of the one or more alignment magnets of the medical device connector complement magnetic poles of the one or more alignment magnets in the mating surface of the relay module connector.

7. The method according to claim 6, wherein the sterile drape comprises a transparent window, and wherein the mating comprises positioning the transparent window between the medical device connector and the relay module connector.

8. The method according to claim 7, wherein the mating further comprises orienting the medical device connector such that an outer perimeter shape of the medical device connector corresponds with an outer perimeter shape of the relay module connector.

9. The method according to claim 6, wherein the mating further comprises orienting the medical device connector such that an outer perimeter shape of the medical device connector corresponds with an outer perimeter shape of the relay module connector.

10. The method according to claim 6, wherein the medical device connector includes an extension tube, and wherein the medical device connector is coupled to an end of the extension tube.

11. The method according to claim 6, wherein placing the relay module on or alongside the patient occurs before placing the sterile drape over the patient.

* * * * *